United States Patent
Jingu et al.

(10) Patent No.: US 10,041,914 B1
(45) Date of Patent: Aug. 7, 2018

(54) DEGASSING DEVICE

(71) Applicant: SHIMADZU CORPORATION, Kyoto-shi, Kyoto (JP)

(72) Inventors: Kumiko Jingu, Kyoto (JP); Keisuke Ogawa, Kyoto (JP); Masato Watanabe, Kyoto (JP); Yusuke Nagai, Kyoto (JP); Masanori Fujiwara, Kyoto (JP); Tomoyuki Yamazaki, Kyoto (JP)

(73) Assignee: SHIMADZU CORPORATION, Kyoto-shi, Kyoto (JP)

( * ) Notice: Subject to any disclaimer, the term of this patent is extended or adjusted under 35 U.S.C. 154(b) by 0 days.

(21) Appl. No.: 15/612,472

(22) Filed: Jun. 2, 2017

(51) Int. Cl.
*G01N 21/00* (2006.01)
*G01N 30/74* (2006.01)
*G01N 21/59* (2006.01)
*G01N 30/02* (2006.01)

(52) U.S. Cl.
CPC ............ *G01N 30/74* (2013.01); *G01N 21/59* (2013.01); *G01N 2030/027* (2013.01)

(58) Field of Classification Search
CPC .. G01N 30/74; G01N 21/59; G01N 2030/027; B01D 15/14
See application file for complete search history.

(56) References Cited

U.S. PATENT DOCUMENTS 5,762,684 A * 6/1998 Hayashi ............. B01D 19/0031 95/24
5,980,742 A * 11/1999 Saitoh ................ B01D 19/0031 210/186

9,188,572 B2 * 11/2015 Nakamura ............. G01N 30/86
2008/0044309 A1 * 2/2008 Yamashita ............. G01N 30/08 422/52

(Continued)

FOREIGN PATENT DOCUMENTS

JP      2012-161723 A      8/2012

OTHER PUBLICATIONS

"Idousou No Dakki, 5. Dakki Houhou, 5-4) Ki-Eki Bunrimaku Wo Mochiita Gen-atsu Dakki (Degassing of Mobile Phase, 5. Degassing Method, 5-4) Reduced-Pressure Degassing Using Gas-Liquid Separation Membrane)", Shimadzu Corporation, [accessed on Jan. 14, 2015].

*Primary Examiner* — Kara E Geisel
*Assistant Examiner* — Maurice Smith
(74) *Attorney, Agent, or Firm* — Sughrue Mion, PLLC

(57) ABSTRACT

A degassing device 2 includes: a built-in absorbance measurement section 28 using an LED light source and measuring the intensity of light transmitted through a mobile phase passing through a flow cell; and a solenoid valve 26 switchable between two states with and without the mobile phase passed through a degassing tube 21. The passage-switching operation by the solenoid valve is performed so as to obtain detection signals of the transmitted light in the absorbance measurement section when the mobile phase drawn from a mobile phase container by a liquid-feeding pump 40 is passed through the degassing tube for degassing as well as when the mobile phase is not passed through the degassing tube for degassing. A signal processor 29 calculates the difference in absorbance based on those detection signals, estimates the degree of degassing based on that difference, and displays the result on a display unit 32.

4 Claims, 3 Drawing Sheets

(56) References Cited

U.S. PATENT DOCUMENTS

2012/0132013 A1\* 5/2012 Glatz .................... G01N 30/20
                     73/863.02
2014/0326664 A1\* 11/2014 Joudrey ................ B01D 15/14
                     210/635
2016/0234904 A1\* 8/2016 Nagai ................ H05B 33/0851

\* cited by examiner

TO INJECTOR

DEGASSING DEVICE

TECHNICAL FIELD

The present invention relates to degassing devices for removing gas and/or bubbles dissolved in liquid. Specifically, the present invention relates to a degassing device that employs a reduced-pressure degassing system using a gas-liquid separation membrane, which is suitable for removing dissolved gas and/or bubbles from a mobile phase in a liquid chromatograph.

BACKGROUND ART

In a typical liquid chromatograph (hereinafter, referred to as "LC"), a mobile phase stored in a mobile phase container is drawn by a liquid-feeding pump and fed to a column through a sample injector. When a sample liquid is injected from the sample injector into the mobile phase at a predetermined timing, the sample liquid is washed out by the mobile phase, to be introduced into the column. While the sample liquid passes through the column, various components in the sample liquid are separated in a time direction so as to be eluted from the outlet of the column. The components contained in the eluate are detected by a detector, such as a photodiode array (PDA) detector, which generate detection signals individually corresponding to the concentrations of the components. Based on the detection signals, a chromatogram is created which indicates the change in the signal intensity along with time.

In such an LC, the mobile phase fed by the liquid-feeding pump under high pressure may contain a large quantity of gas that may cause bubbles to occur in the column or a cell in the detector. Such bubbles are one of the factors for a deformation of the peak or an occurrence of spike noises in the chromatogram. Furthermore, a change in the quantity of gas (mainly oxygen) dissolved in the mobile phase that arrives at the detector also causes a fluctuation or drift of the baseline in the chromatogram. In addition, if bubbles occur in the mobile phase container or other locations and are fed into the liquid-feeding pump, those bubbles may cause defectiveness in the liquid-feeding operation by the pump, causing a change in the retention time of the peak or other problems. In order to reduce such adverse effects on the analysis results, a conventional LC includes a degassing device in the passage between the mobile phase container and the liquid-feeding pump, for removing air and/or bubbles dissolved in the mobile phase.

There are several systems for degassing. One of the widely used systems is a reduced-pressure degassing system using a gas-liquid separation membrane. As disclosed in Patent Literature 1 and Non Patent Literature 1, a degassing device that employs such a system (hereinafter, a degassing device that employs the reduced-pressure degassing system using a gas-liquid separation membrane is simply referred to as a "degassing device") includes a degassing tube contained in a vacuum chamber evacuated (or pressure-reduced) by a vacuum pump, which tube is made of a gas-permeable material (such as polytetrafluoroethylene (PTFE)-based synthetic resin) that allows gas to pass through while preventing the passage of liquid. When a mobile phase drawn from the mobile phase chamber flows through the degassing tube, the air dissolved in the mobile phase is extracted into a vacuum atmosphere through the wall surface of the degassing tube made of the gas-permeable material. Thus, the air in the mobile phase is removed.

If an abnormality has been found in a measurement result obtained by an LC system using the aforementioned degassing device, the cause of the abnormality may possibly be degradation in the degassing performance of the degassing device. Meanwhile, when high measurement accuracy is required, a high level of degassing performance is necessary since even a few bubbles can cause problems. In view of the above, it may be necessary to verify the degassing performance of the degassing device at an appropriate timing. In a typical method for verifying the degassing performance of the degassing device, the absorbance of the mobile phase is measured in each of the two cases where the mobile phase is passed through the degassing device and where the mobile phase is not passed through, using an ultraviolet (UV) visible light spectrophotometer, and the degassing performance is determined based on a change in the absorbance between the two cases.

CITATION LIST

Patent Literature

Patent Literature 1: JP 2012-161723 A

Non-Patent Literature

Non Patent Literature 1: "Idousou No Dakki, 5. Dakki Houhou, 5-4) Ki-Eki Bunrimaku Wo Mochiita Gen-atsu Dakki (Degassing of Mobile Phase, 5. Degassing Method, 5-4) Reduced-Pressure Degassing Using Gas-Liquid Separation Membrane)" Shimadzu Corporation, [accessed on Jan. 14, 2015], the Internet <URL: http://www.an.shimadzu.co.jp/hplc/support/lib/lctalk/s5/054.htm>

SUMMARY OF INVENTION

Technical Problem

The use of a separate UV spectrophotometer or similar device for verifying the degassing performance of a degassing device built in an LC system makes the entire system large in size and results in a large burden of cost. In addition, in order to perform the measurement for both the case where the mobile phase is passed through the degassing device and the case where the mobile phase is not passed through, the passage for the mobile phase needs to be changed, which is a troublesome task and consumes time and labor. Accordingly, the degassing performance of a degassing device built in an LC system has hardly been verified.

The present invention has been made in view of such problems. An objective of the present invention is to provide a degassing device which allows for easy and accurate verification of the degassing performance by users or other individuals without requiring them to prepare a UV spectrophotometer or similar device or perform a cumbersome task for changing the passages.

Solution to Problem

The present invention developed for solving the previously described problem is a degassing device including: a chamber evacuated by a vacuum pump; and a degassing tube housed in the chamber and made of a gas-permeable material allowing gas to pass through while preventing liquid from passing through, the degassing tube having a wall surface through which gas contained in liquid flowing through the degassing tube is taken out to be discharged; and the degassing device further including:

a) an absorbance measurement section that includes a flow cell through which the liquid flows, a light-casting unit using a semiconductor light-emitting element as a light source for casting measurement light into the flow cell, and a photodetector for detecting light resulting from transmission of the measurement light through the flow cell;

b) a passage-switching section switchable between a first passage through which the liquid introduced into the degassing device flows into the flow cell after passing through the degassing tube and a second passage through which the liquid introduced into the degassing device flows into the flow cell without passing through the degassing tube; and c) a signal processor for calculating a piece of information reflecting degassing performance or for determining the degassing performance, based on a first detection signal obtained by the photodetector of the absorbance measurement section with the first passage formed by the passage-switching section, and a second detection signal obtained by the photodetector of the absorbance measurement section with the second passage formed by the passage-switching section.

In the degassing device according to the present invention, the semiconductor light-emitting element used as the light source in the absorbance measurement section is selected from a light-emitting diode (LED), a super luminescent diode (SLD), and a laser diode (LD). Such a semiconductor light-emitting element typically has an emission spectrum with a narrow peak width. Thus, light from the semiconductor light-emitting element can be directly used as the measurement light without being turned into monochromatic light through an expensive monochromator. Such a semiconductor light-emitting element is remarkably small in size and inexpensive in comparison with a light source used in a typical UV spectrophotometer, such as a deuterium lamp or a xenon flash lamp. Thus, the absorbance measurement section in the degassing device according to the present invention can be remarkably small in size and inexpensive in comparison with the one used in a typical UV spectrophotometer, so as to be easily contained inside the housing of the degassing device.

In the degassing device according to another aspect of the present invention, the passage-switching section typically includes a switching valve, such as a solenoid valve. When the first passage is formed by the passage-switching section, liquid such as a mobile phase that is used for the LC and is introduced into the degassing device by the liquid-feeding operation by another liquid-feeding pump, for example, passes through the degassing tube, and finally flows into the flow cell after undergoing the degassing process. When the second passage is formed by the passage-switching section, liquid such as a mobile phase that is introduced into the degassing device due to the liquid-feeding operation by the liquid-feeding pump flows into the flow cell without passing through the degassing tube, i.e., without undergoing the degassing process.

The larger the quantity of air and/or bubbles dissolved in liquid that flows through the flow cell is, the higher the absorbance of light by the liquid becomes. Accordingly, based on the detection signals obtained with the photodetector of the absorbance measurement section in the state where the first passage is formed as well as those obtained by the same photodetector in the state where the second passage is formed, the signal processor calculates, for example, the difference in absorbance between these states. The signal processor thus calculates an index value indicating the degree of degassing from the measured difference in the absorbance by using an approximate relation between the degree of degassing and the absorbance difference that has been experimentally calculated in advance, and displays the obtained value on a display unit, for example. Alternatively, the signal processor may compare the index value indicating the degree of degassing with a predetermined threshold value. When the index value is below the threshold value, the signal-processor may determine that the degassing is not sufficient, and display the determination result or issue a warning.

In one mode of the degassing device according to the present invention, the flow cell in the absorbance measurement section has an inlet end and an outlet end that are respectively connected to two passages each of which has an open end at the other end, the first passage and the second passage formed by the passage-switching section share a common passage located downstream of the degassing tube and having an open end, and the open ends are connectable with each other or with the liquid-feeding pump through a pipeline outside the degassing device so as to form a passage through which the liquid having passed through the degassing tube flows into the flow cell.

With this configuration, the connection of the pipelines located outside the device can be changed so as to switch the entire configuration between the state where the absorbance measurement section including the flow cell is located upstream of the liquid-feeding pump and the state where the same unit is located downstream of the pump. Specifically, the passage can be configured in such a manner that liquid that has passed through the degassing tube flows through one external pipeline to the suction port of the liquid-feeding pump, and the liquid discharged from the ejection port of the liquid-feeding pump flows through another external pipeline to the flow cell. Alternatively, the passage can also be configured in such a manner that liquid that has passed through the degassing tube flows into the flow cell after passing through one external pipeline, and the liquid that has passed through the flow cell flows through another external pipeline to the liquid-feeding pump. In a typical LC system, the liquid-feeding pump that feeds the mobile phase to a column is controlled so as to diminish pulsation in the passage on the ejection side of the pump. Accordingly, arranging the absorbance measurement section on the downstream side of the liquid pump is preferable so as to diminish the pulsation of the liquid flowing into the flow cell and improve the accuracy of the absorbance measurement.

The degassing device according to the present invention may further include, in addition to the aforementioned passage-switching section, a second passage-switching section switchable between a passage for making the liquid fed through the first and the second passages flow through the flow cell in the absorbance measurement section and a passage for making the same liquid flow to a point downstream of the flow cell without passing through the flow cell.

With this configuration, when, for example, a normal measurement is carried out in the LC system, the passage is formed by the operation of the second passage-switching section in such a manner that the mobile phase flows to a point downstream of the flow cell without passing through the flow cell. Accordingly, the degassed mobile phase can be fed to the sample injector or the like without passing through the flow cell.

Advantageous Effects of the Invention

In the degassing device according to the present invention, the degassing performance can be verified by the degassing device alone, without preparing another measurement device, such as a UV spectrophotometer. This prevents the device and system from being large in scale for verifying the degassing performance, thereby reducing the cost. Furthermore, the degassing device according to the present invention does not require any cumbersome task for manually changing the passages to verify the degassing performance. This reduces the measurement time and the burden on a person in charge of the operation, such as a user or a field engineer. In addition, the degassing device according to the present invention allows easy verification of the degassing performance at any time, e.g. before a measurement of a sample or during an intermission of the measurement, making it possible to promptly detect deficiencies in the degassing. This prevents measurements from being uselessly performed under defective degassing, and also improves maintainability of the device.

DESCRIPTION OF EMBODIMENTS

An embodiment of the degassing device according to the present invention is hereinafter described, with reference to the drawings.

Figure 1:
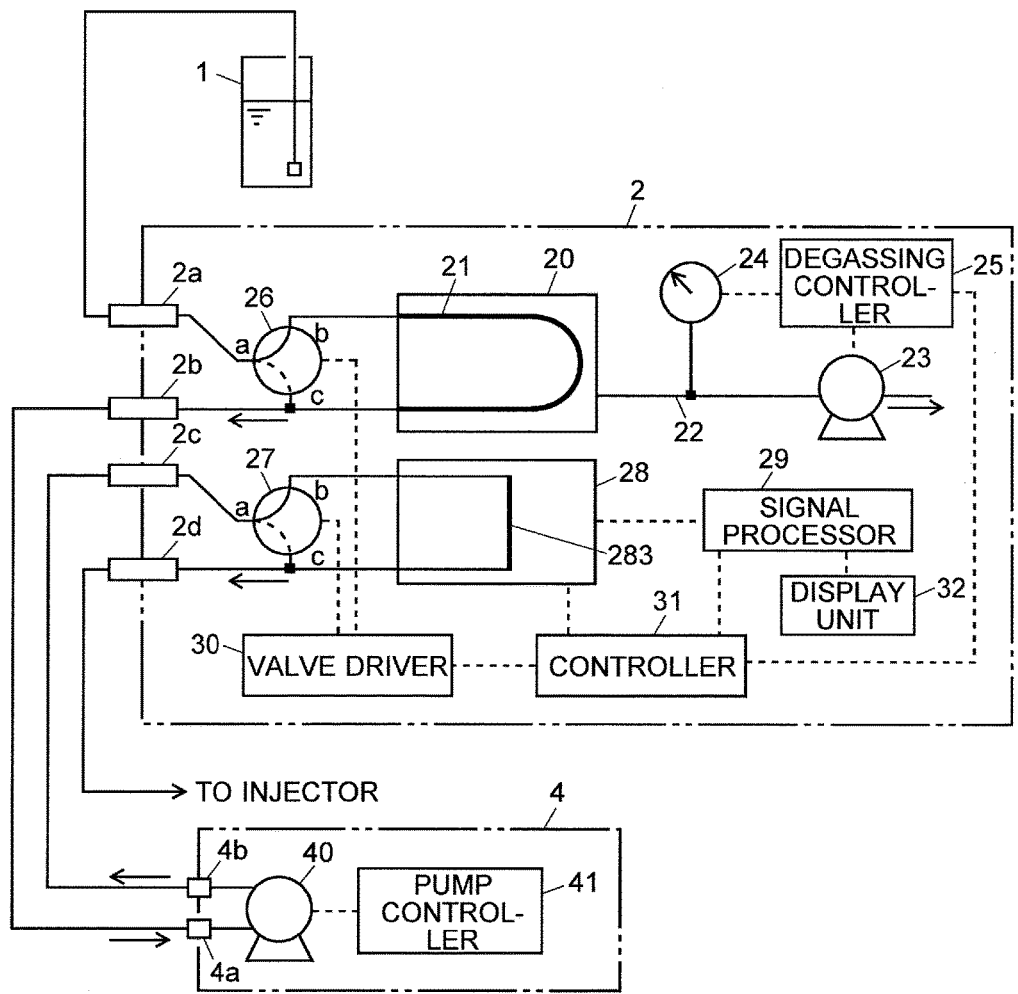
FIG. 1 is a schematic configuration diagram showing a liquid-feeding unit of an LC including a degassing device according to an embodiment of the present invention.
Figure 2:
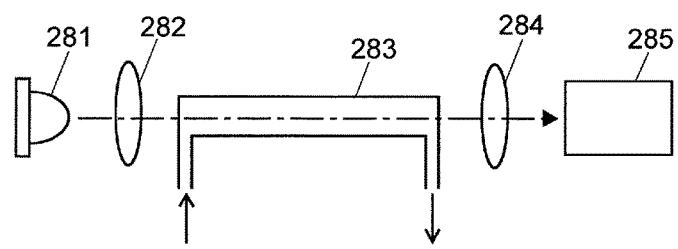
FIG. 2 is a schematic configuration diagram showing an absorbance measurement section in the degassing device shown in FIG. 1.

FIG. 1 is a schematic configuration diagram showing a liquid-feeding unit of an LC including the degassing device according to the present embodiment. FIG. 2 is a schematic configuration diagram showing an absorbance measurement section in the degassing device shown in FIG. 1.

A degassing device 2 according to the present embodiment includes: a box-shaped, hermetically sealable vacuum chamber 20; an evacuation passage 22 having one end connected to the vacuum chamber 20; a vacuum pump 23 provided in the evacuation passage 22; a pressure sensor 24 connected to the evacuation passage 22 between the vacuum chamber 20 and the vacuum pump 23; and a degassing controller 25 that controls the operation of the vacuum pump 23 according to the pressure detected by the pressure sensor 24. The vacuum chamber 20 contains a degassing tube 21 made of a gas-permeable material that allows gas to pass through while preventing liquid to pass through. The degassing tube 21 has the two ends respectively connected to port b and port c of a first solenoid valve 26. The first solenoid valve 26 is a 2-position/3-port valve that is switchable between a passage which connects ports a to b and a passage which connects ports a to c. Ports a and c of the first solenoid valve 26 are respectively connected to the passage connection ends 2a and 2b of the degassing device 2.

The degassing device 2 further includes an absorbance measurement section 28 and a signal processor 29 that processes detection signals obtained in the absorbance measurement section 28. The absorbance measurement section 28 includes a flow cell 283 having its two ends respectively connected to ports b and c of a second solenoid valve 27, which is a 2-position/3-port valve like the first magnetic valve 26. The second solenoid valve 27 has ports a and c respectively connected to the passage connection ends 2c and 2d of the degassing device 2. The degassing device 2 further includes: a valve driver 30 for operating the first and the second solenoid valves 26 and 27; a controller 31 that controls operations of the valve driver 30, absorbance measurement section 28, and degassing controller 25; a display unit 32 annexed to the signal processor 29; and other units.

In configuration example shown in FIG. 1, a mobile phase container 1 holding a mobile phase is connected to the passage connection end 2a of the degassing device 2, and a liquid-feeding unit 4 that includes a liquid-feeding pump 40 and a liquid-feeding pump controller 41 has a suction-side connection end 4a and an ejection-side connection end 4b respectively connected to the passage connection ends 2b and 2c of the degassing device 2. The passage connection end 2c of the degassing device 2 is connected to a sample injector (automatic sampler), which is not shown.

As shown in FIG. 2, the absorbance measurement section 28 includes a light-casting unit 281 using a light-emitting diode (LED) as its light source, a condensing lens 282, a flow cell 283 through which the mobile phase passes, a condensing lens 284, and a photodetector 285. The LED is, for example, a deep ultraviolet LED which emits light with the highest-intensity peak located at a central wavelength of approximately 210 nm. An LED typically has an emission peak with such a narrow wavelength range that allows the emitted light to be directly used as the measurement light. Additionally, an optical filter acting as a short pass filter may be used in combination with the LED to remove unnecessary light. A light beam emitted from the light-casting unit 281 and focused by the condensing lens 282 is cast, as the measurement light, into the flow cell 283 through which the mobile phase flows. While passing through the flow cell 283, the measurement light is absorbed by a magnitude which mainly depends on the quantity of air and/or bubbles dissolved in the mobile phase in the flow cell 283. The light that has undergone the absorption and has passed through the flow cell 283 is incident on the photodetector 285 via the condensing lens 284. The photodetector 285 generates detection signals corresponding to the amount of incident light.

The absorbance measurement section 28 needs no monochromator for extracting monochromatic light, unlike conventional and typical UV spectrophotometers, and has an extremely small light source. Accordingly, the absorbance measurement section 28 can be designed within the dimensions of, for example, about 40(W)×50(D)×30(H) mm, and thus can be contained in a single housing together with the vacuum chamber 20 and other components.

In a normal measurement in the LC system, the valve driver 30 under the command of the controller 31 switches the first solenoid valve 26 to form a passage that connects port a with port b, and also switches the second magnetic valve 27 to form a passage that connects port a with port c. The liquid-feeding pump controller 41 energizes the liquid-feeding pump 40 to draw and eject the mobile phase at a constant flow rate. With this operation by the liquid-feeding pump 40, the mobile phase drawn from the mobile phase container 1 is introduced into the degassing device 2, and flows through the degassing tube 21. The mobile phase temporarily flows out of the degassing device 2 to pass through the liquid-feeding pump 40, and then is once again introduced into the degassing device 2. The mobile phase then flows out of the degassing device 2 without passing through the absorbance measurement section 28, and is fed to the sample injector.

The degassing controller 25 operates the vacuum pump 23 so that the pressure detected by the pressure sensor 24 is maintained at a predetermined value. By this operation, the pressure inside the vacuum chamber 20 is reduced to a predetermined level. Accordingly, the air dissolved in the mobile phase passing through the degassing tube 21 is extracted through the wall surface of the degassing tube 21 into the vacuum chamber 20, to be eventually discharged through the evacuation passage 22. Thus, the air is removed from the mobile phase, and the degassed mobile phase is fed to the sample injector.

When the degassing performance of the degassing device 2 is verified, the valve driver 30 under the command of the controller 31 switches the second magnetic valve 27 to form a passage that connects port a with port b. In the first solenoid valve 26, the passage between ports a and b is first formed for a predetermined time period t. After the lapse of the predetermined time t, the first magnetic valve 26 is switched to form a passage that connects port a with port c. The liquid-feeding pump 40 and the vacuum pump 23 operate in the same manner as in the previously mentioned measurement.

During the predetermined time period t, the mobile phase drawn from the mobile phase container 1 is introduced into the degassing device 2, and flows through the degassing tube 21, due to the operation of the liquid-feeding pump 40. Then, the mobile phase temporarily flows out of the degassing device 2 and is once again introduced into the degassing device 2 after passing through the liquid-feeding pump 40. The mobile phase flows through the absorbance measurement section 28, and then flows out of the degassing device 2, to be eventually fed to the sample injector. Meanwhile, in the absorbance measurement section 28, the measurement light emitted from the light-casting unit 281 is cast into the flow cell 283, and the light that passes through the flow cell 283 reaches the photodetector 285, which generates detection signals. As aforementioned, the mobile phase passes through the degassing tube 21, and the air dissolved in the mobile phase is removed in the decompressed vacuum chamber 20, so that the degassed mobile phase flows in the flow cell 283. Thus, the detection signals obtained in the absorbance measurement section 28 at this time reflect the absorbance of light by the degassed mobile phase. Hereinafter, these detection signals are referred to as "detection signals with degassing".

After the lapse of the predetermined time period t, the mobile phase being drawn from the mobile phase container 1 by the operation of the liquid-feeding pump 40 is still introduced into the degassing device 2. However, this time, the mobile phase does not flow through the degassing tube 21; it is immediately sent to and passes through the liquid-feeding pump 40, and then is once again introduced into the degassing device 2. After flowing through the absorbance measurement section 28, the mobile phase flows out of the degassing device 2, to be eventually fed to the sample injector. This means that the mobile phase that is not degassed flows through the flow cell 283 after the lapse of the predetermined time period t. Thus, the detection signals obtained in the absorbance measurement section 28 at this time reflect the absorbance of light by the mobile phase that is not degassed. Hereinafter, these detection signals are referred to as "detection signals without degassing".

The larger the quantity of air or bubbles dissolved in the mobile phase is, the more the light to be absorbed becomes. With this, the intensity of the transmitted light that reaches the photodetector 285 decreases. Therefore, the higher the degassing performance of the degassing tube 21 during the passage of the mobile phase is, the larger the difference becomes between the absorbance determined from the detection signals with degassing and the absorbance determined from the detection signals without degassing. Accordingly, the difference in absorbance between the detection signals with and without degassing indicates the degree of degassing.

Figure 4:
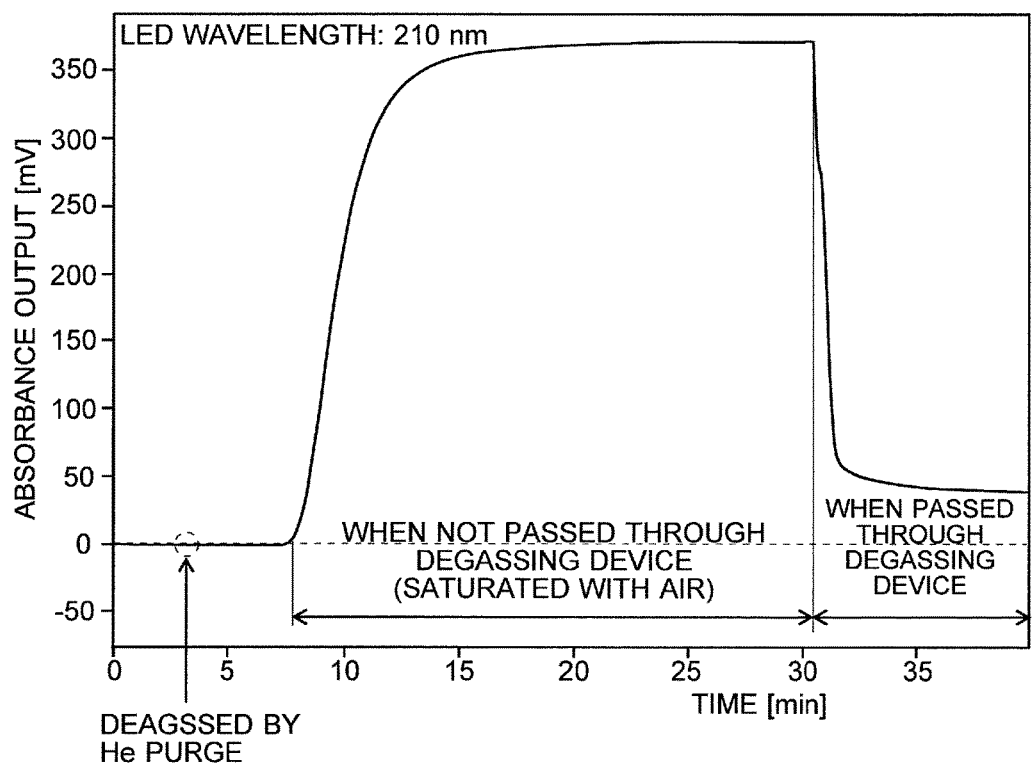
FIG. 4 is a graph showing an example of measured absorbance.

FIG. 4 is a graph showing an example of actually measured absorbance. The horizontal axis indicates elapsed time, and the vertical axis indicates output of the absorbance calculated from the detection signals obtained with the photodetector. During a time period from 0 to 8 minutes, helium (He) bubbling is continuously performed in the mobile phase container to purge the air in the mobile phase. Accordingly, the absorbance output during this period can be recognized as the absorbance in a state where little air is dissolved in the mobile phase. After the lapse of 8-minute period, air bubbling is continuously performed in the mobile phase container to saturate the mobile phase with air. At this occasion, the absorbance is high when the mobile phase is not passed through the degassing tube. In contrast, when the mobile phase is passed through the degassing tube and degassed, the absorbance significantly decreases, showing a noticeable difference from the absorbance measured without degassing. Accordingly, it is apparent that the degree of degassing can be estimated from the difference in absorbance.

In view of the above, the signal processor 29 calculates the difference in absorbance between the degassed state and non-degassed state from the detection signals with and without degassing, and further calculates an estimated degree of degassing from the calculated difference in absorbance. To calculate the estimated degree of degassing from the difference in absorbance, a table or formula can be used which indicates the relation between the degree of degassing and the difference in absorbance that has been experimentally calculated in advance. Users do not need to prepare such a table or formula; device manufacturers may set these tables or formulas in advance. The signal processor 29 shows the user the calculated value of the estimated degree of degassing by displaying those values on the display unit 32.

In addition to or instead of displaying the estimated degree of degassing, the signal processor may also compare the estimated degree of degassing with a predetermined threshold value. If the estimated degree of degassing is below the threshold value, i.e. if it is assumed that the degassing performance is insufficient, a warning may be issued by display or sound. The predetermined threshold value may be specified in advance, or alternatively, an appropriate value may be set by users as needed.

In the LC system using the degassing device 2 according to the present embodiment, the degassing performance of the degassing device 2 can be easily verified at any timing. The verification of the degassing performance requires neither the preparation of an additional device (e.g. UV spectrophotometer) nor the manual changing of the passages. This reduces the time required for such verification.

Figure 3:
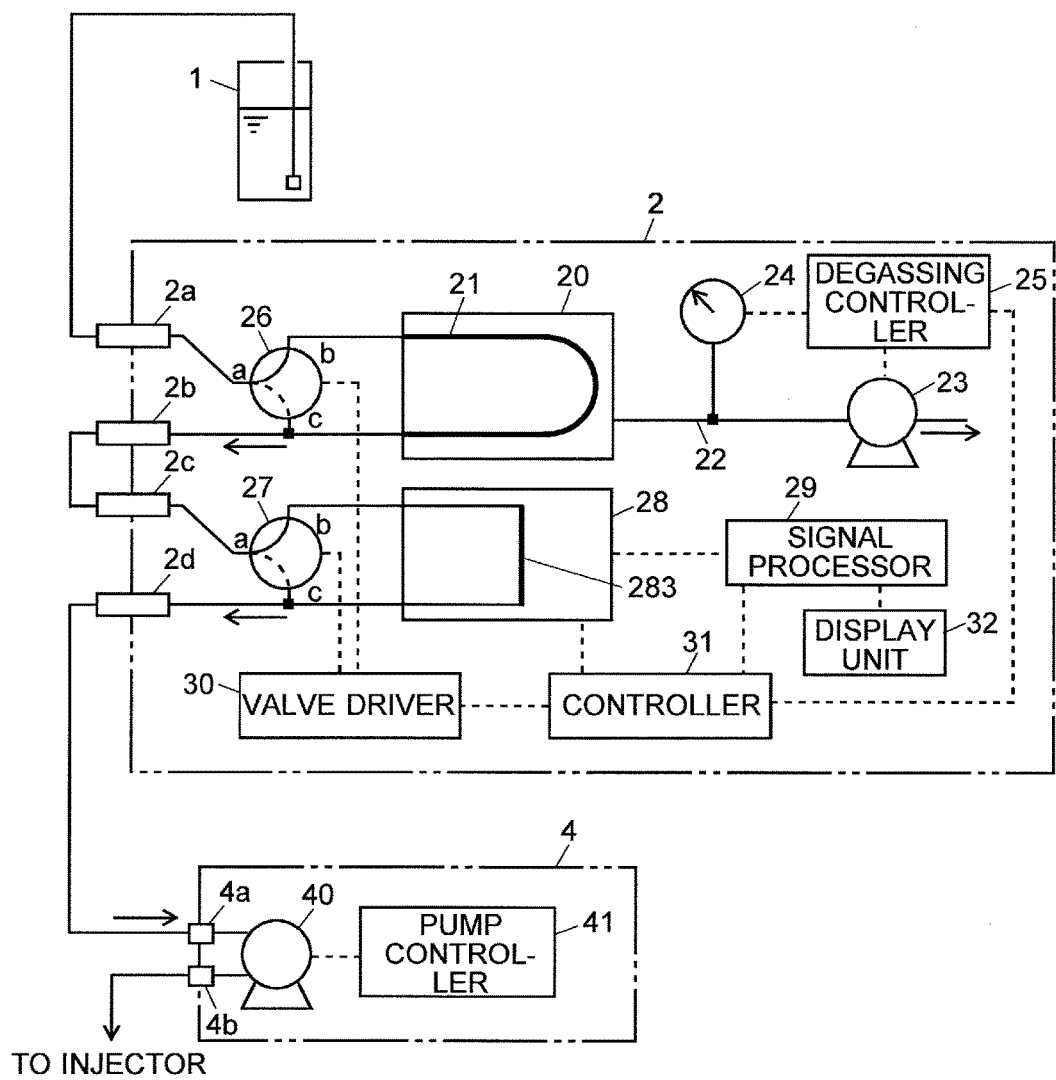
FIG. 3 is a schematic configuration diagram showing another example of the liquid-feeding unit of the LC including the degassing device according to the embodiment of the present invention.

Although the absorbance measurement section 28 is arranged on the downstream side, i.e., on the ejection side, of the liquid-feeding pump 40 in the configuration shown in FIG. 1, the absorbance measurement section 28 can be arranged on the upstream side, i.e., on the suction side, of the liquid-feeding pump 40. FIG. 3 is a schematic configuration diagram of a liquid-feeding unit in the LC in which the degassing device 2 shown in FIG. 1 is used, with the pipelines connected in a different way to the passage connection ends 2a to 2d of the degassing device 2. In this configuration, the mobile phase that has passed through the degassing tube 21 is introduced into the absorbance measurement section 28. After passing through the absorbance measurement section 28, the mobile phase is fed to the sample injector via the liquid-feeding pump 40. The operation for verifying the degassing performance of the degassing device 2 in the present configuration is completely the same as in the previously described case.

In typical LC systems, the operation of the liquid-feeding pump is controlled so as to diminish pulsation on the ejection side of the liquid-feeding pump, in order to restrain the pulsation of the mobile phase flowing into the column via the sample injector. Accordingly, configuring the passage in such a manner that the absorbance measurement section 28 is located downstream of the liquid-feeding pump 40, as in the configuration example shown in FIG. 1, more effectively diminishes the pulsation of the mobile phase flowing into the flow cell 283 in the absorbance measurement section 28 and thereby reduces the fluctuation in absorbance due to the pulsation.

The aforementioned embodiment is merely an example of the present invention. It is apparent that any modification, correction, or addition within the scope of the present invention is included in the scope of claims of the present application.

For example, the LED used as a light source of the absorbance measurement section 28 in the aforementioned embodiment may be replaced by a different type of semiconductor light-emitting element other than the LED. Its emission wavelength is not particularly limited as long as the absorbance can be measured.

REFERENCE SIGNS LIST

1 . . . Mobile Phase Container
2 . . . Degassing Device
20 . . . Vacuum Chamber
21 . . . Degassing Tube
22 . . . Evacuation Passage
23 . . . Vacuum Pump
24 . . . Pressure Sensor
25 . . . Degassing Controller
26, 27 . . . Solenoid Valve
28 . . . Absorbance Measurement Section
281 . . . Light-Casting Unit
282, 284 . . . Condensing Lens
283 . . . Flow Cell
285 . . . Photodetector
29 . . . Signal Processor
30 . . . Valve Driver
31 . . . Controller
32 . . . Display Unit
2a, 2b, 2c, 2d . . . Passage Connection End
4 . . . Liquid-Feeding Unit
40 . . . Liquid-Feeding Pump
41 . . . Liquid-Feeding Pump Controller
4a . . . Suction-Side Connection End
4b . . . Ejection-Side Connection End

The invention claimed is:

1. A degassing device comprising: a chamber evacuated by a vacuum pump; and a degassing tube housed in the chamber and made of a gas-permeable material allowing gas to pass through while preventing liquid from passing through, the degassing tube having a wall surface through which gas contained in liquid flowing through the degassing tube is taken out to be discharged; and the degassing device further comprising:

a) an absorbance measurement section that includes a flow cell through which the liquid flows, a light-casting unit using a semiconductor light-emitting element as a light source for casting measurement light into the flow cell, and a photodetector for detecting light resulting from transmission of the measurement light through the flow cell;

b) a passage-switching section switchable between a first passage through which the liquid introduced into the degassing device flows into the flow cell after passing through the degassing tube and a second passage through which the liquid introduced into the degassing device flows into the flow cell without passing through the degassing tube; and c) a signal processor for calculating a piece of information reflecting degassing performance or for determining the degassing performance, based on a first detection signal obtained by the photodetector of the absorbance measurement section with the first passage formed by the passage-switching section, and a second detection signal obtained by the photodetector of the absorbance measurement section with the second passage formed by the passage-switching section.

2. The degassing device according to claim 1, wherein: the flow cell in the absorbance measurement section has an inlet end and an outlet end that are respectively connected to two passages each of which has an open end at another end, the first passage and the second passage formed by the passage-switching section share a common passage located downstream of the degassing tube and having an open end, and the open ends are connectable with each other or with the liquid-feeding pump through a pipeline outside the degassing device so as to form a passage through which the liquid having passed through the degassing tube flows into the flow cell.

3. The degassing device according to claim 2, further comprising a second passage-switching section switchable between one passage for making the liquid fed through the first and the second passages flow through the flow cell in the absorbance measurement section, and another passage for making the same liquid flow to a point downstream of the flow cell without passing through the flow cell.

4. The degassing device according to claim 1, further comprising a second passage-switching section switchable between one passage for making the liquid fed through the first and the second passages flow through the flow cell in the absorbance measurement section, and another passage for making the same liquid flow to a point downstream of the flow cell without passing through the flow cell.

* * * * *